United States Patent
Molema et al.

(10) Patent No.: US 8,028,708 B2
(45) Date of Patent: Oct. 4, 2011

(54) APPLIANCE FOR PERSONAL CARE WITH AUTOMATIC FLUID DISPENSER

(75) Inventors: Jeroen Molema, Drachten (NL); Anke Sinnema, Drachten (NL); Wilko Westerhof, Drachten (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 871 days.

(21) Appl. No.: 11/908,774

(22) PCT Filed: Mar. 15, 2006

(86) PCT No.: PCT/IB2006/050806
§ 371 (c)(1),
(2), (4) Date: Sep. 14, 2007

(87) PCT Pub. No.: WO2006/100627
PCT Pub. Date: Sep. 28, 2006

(65) Prior Publication Data
US 2008/0189951 A1    Aug. 14, 2008

(30) Foreign Application Priority Data
Mar. 21, 2005  (EP) ..................................... 05102216

(51) Int. Cl.
*A45D 27/00*  (2006.01)
(52) U.S. Cl. ...................................................... 132/292
(58) Field of Classification Search .................. 132/112, 132/292; 30/41.5, 56, 538; 222/52, 56, 23, 222/639, 55, 175, 630, 63, 613, 631, 333; 239/93, 101, 11; 118/663, 683, 715, 696, 118/699, 712; 700/47, 44, 283
See application file for complete search history.

(56) References Cited

U.S. PATENT DOCUMENTS

| | | | |
|---|---|---|---|
| 3,176,392 A | 4/1965 | Gwinn | |
| 4,031,618 A | 6/1977 | Mansfield | |
| 5,927,290 A * | 7/1999 | Thiruppathi | 132/116 |
| 6,126,669 A | 10/2000 | Rijken | |
| 6,312,436 B1 | 11/2001 | Rijken et al. | |
| 6,513,534 B1 * | 2/2003 | Sofer et al. | 132/112 |
| 6,612,819 B1 | 9/2003 | Furst et al. | |
| 6,723,077 B2 * | 4/2004 | Pickup et al. | 604/305 |
| 2005/0021051 A1 * | 1/2005 | Saitou et al. | 606/133 |
| 2006/0208001 A1 * | 9/2006 | Gross | 222/190 |

FOREIGN PATENT DOCUMENTS

| | | |
|---|---|---|
| EP | 0125989 A2 | 11/1984 |
| FR | 2613975 | 10/1988 |
| WO | 2003068466 A1 | 8/2003 |
| WO | 2003089201 A1 | 10/2003 |
| WO | 2004050313 A1 | 6/2004 |
| WO | 2006099977 | 10/2005 |

* cited by examiner

*Primary Examiner* — Todd E Manahan
*Assistant Examiner* — Brianne O'Neill
(74) *Attorney, Agent, or Firm* — Sherry Womack

(57) ABSTRACT

An appliance for personal care, such as skin, dental or hair treatment, comprising a dispensing structure (30) for automatically dispensing a fluid. The dispensing structure (30) includes a fluid reservoir (10), a discharge opening (11) and a fluid drive structure (9, 12, 15, 16, 17, 19, 20) for driving the fluid to be dispensed from the reservoir (10) to and out of said discharge opening (11) in accordance with a dispensing rate/time profile ($S_x$). The fluid drive structure (9, 12, 15, 16, 17, 19, 20) is arranged for spurting at least once during said dispensing operation for squirting an additional quantity of the fluid to and out of the discharge opening (11) in addition to the fluid being dispensed in accordance with said dispensing rate/time profile ($S_x$).

10 Claims, 4 Drawing Sheets

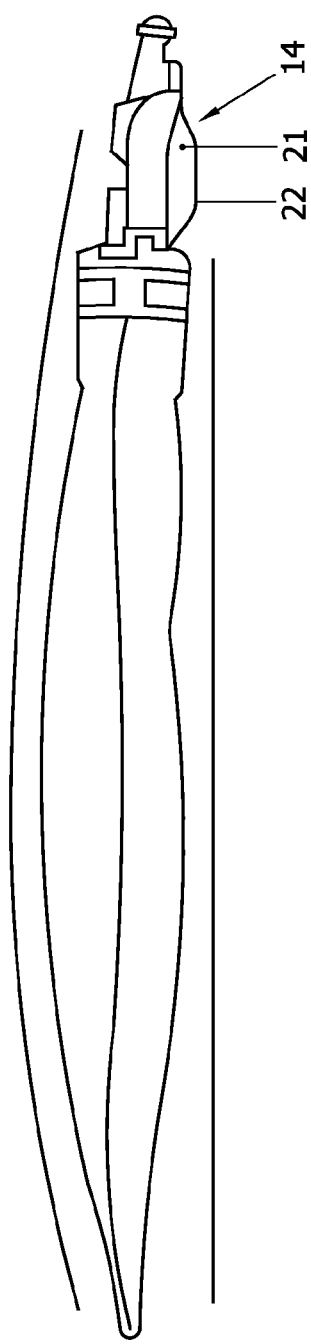
FIG. 4
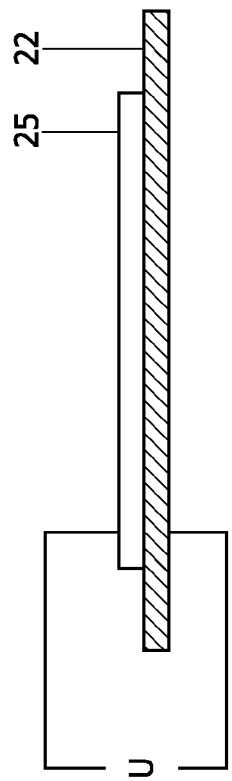
FIG. 4A
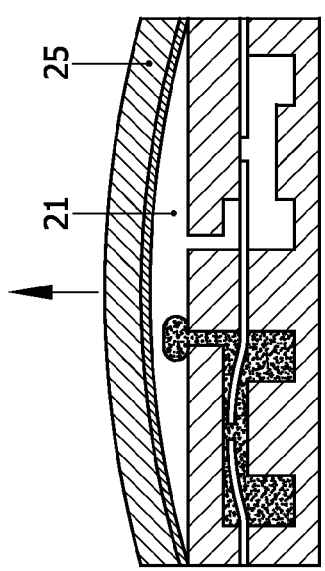
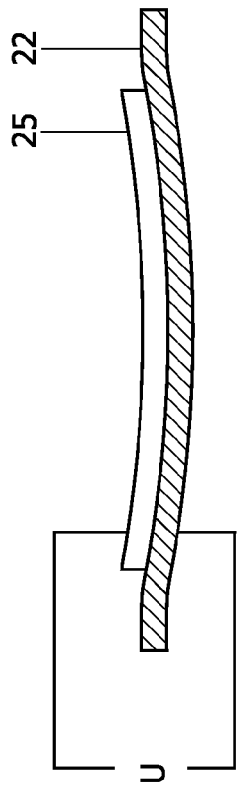
FIG. 4B
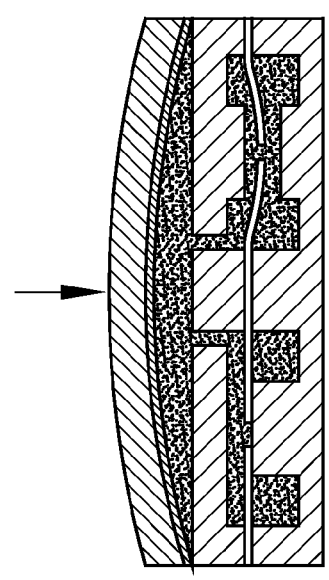

APPLIANCE FOR PERSONAL CARE WITH AUTOMATIC FLUID DISPENSER

The invention relates to an appliance for personal care, such as a shaver, toothbrush or hairdryer, including a dispensing structure for dispensing a fluid to a body part to be treated in order to facilitate or enhance treatment thereof.

An example of such an appliance is a shaver as disclosed in U.S. Pat. No. 3,176,392. In this document, it is disclosed that the flow of the fluid may be controlled by various means such as an On-Off valve, a variable flow control means, or a metering device, which delivers a known quantity each time it is actuated. It is further disclosed that actuation of the flow control means may be achieved by actuating the valve in response to pressure on a roller associated with the shaver or by actuating a liquid dispensing valve via a valve actuating lever. Another example of such an appliance is a shaver as disclosed in U.S. Pat. No. 6,126,669. This shaver is equipped with a reservoir for holding a fluid in the form of a shaving lotion or gel, and with a diaphragm pump for automatically dispensing the fluid onto the skin. The diaphragm pump is driven by a solenoid via an actuator. A control circuit supplies a current pulse at regular intervals through the coil of the solenoid so that a regular supply of fluid is obtained.

To achieve the proper dosage of the fluid throughout the treatment, the dispensing means that cause a quantity of the fluid to be supplied to the treatment area, need to be activated quite frequently. Moreover, a lack of the fluid is generally experienced before actuation, while an excess of the fluid is generally experienced briefly after the activation. Where a fluid is automatically supplied continuously or at regular intervals, the need of operating the dispenser during treatment is avoided. However, at least at some portions of the treatment area, the dosage of the fluid is often too high or too low.

It is an object of the invention to reduce the extent to which users experience lack or scarceness of fluid dispensed from an appliance for personal care, without the necessity of frequent operations to actuate the dispensing means.

According to the present invention this object is achieved by providing an appliance according to claim 1.

The present invention allows an additional dosage of fluid by causing the fluid drive structure to spurt and thereby squirt an additional quantity of the fluid out of the reservoir during a limited period of time. Thereby, lack or scarceness of fluid during treatment is counteracted. Moreover, by squirting the fluid at the right moment and by keeping effective the dispensing rate/time profile during non-spurting dispensing operation, effective treatment conditions are ensured, while waste of fluid is avoided since the additional fluid is only dispensed for a limited period of time and the normal dispensing rate/time profile can be relatively lean, without causing unavoidable lack or scarceness of fluid in the area or areas to be treated.

Particular embodiments of the invention are set forth in the dependent claims.

Further features, effects and details of embodiments of the invention are described below with reference to the accompanying schematical drawings, wherein:

FIG. 4 is an enlarged view of FIG. 1, showing a reservoir with a cartridge and a pump, as well as an alternative actuator for activating said pump;

FIGS. 4a and 4b show an alternative power supply to the pump.

In this description, a shaver according to the invention is described. However, the invention is not limited to shavers, but may also be embodied in other personal care appliances for treatment of a body part, wherein a fluid is dispensed to enhance the treatment, such as an epilator, a toothbrush or a hairstyler. The fluid to be dispensed may for instance be a gas or vapor, a liquid, a paste or a gel containing a cleaning or polishing agent, steam, a skin treatment agent, a disinfecting agent, perfume or a hairstyling agent, such as wax or a fixating or coloring agent. For the purpose of shaving, the fluid may for instance be any form of liquid, gel or paste which reduces the friction between the head and the face and which may be generally characterized as a glide agent.

Figure 1:
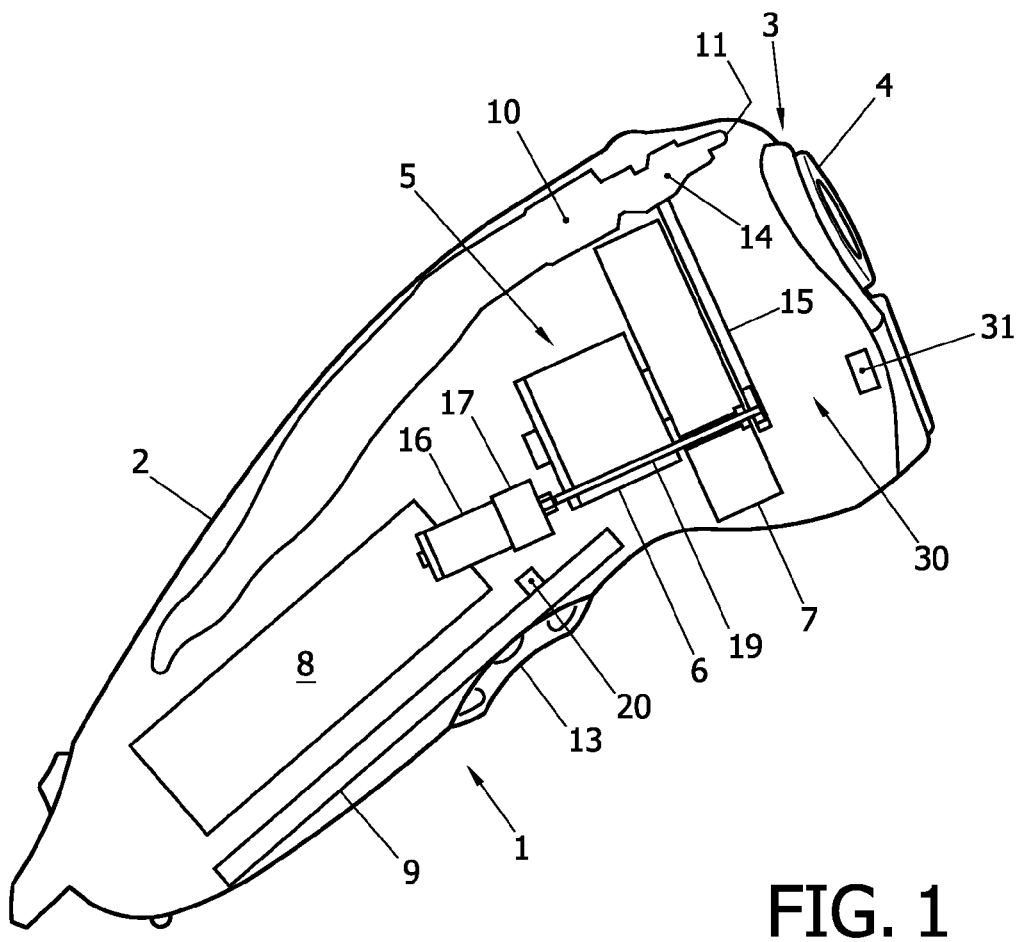
FIG. 1 is a cross-sectional view of an example of an appliance according to the invention.

The shaver 1 shown in FIG. 1 comprises a housing 2 and a shaving head 3, which is hinged or otherwise removably connected to the housing 2. The shaving head 3 is provided with cutters 4, driven by a main drive system 5, which is accommodated in the housing 2. The main drive system 5 comprises a main motor 6, a transmission 7, power supply circuitry 8 including for instance a battery and conductors, a main motor control circuit 9 and a power switch 13. The power switch 13 may have other functions as well, as will be discussed later.

The housing 2 furthermore accommodates a dispensing structure 30. According to this example, the dispensing structure 30 includes a reservoir 10 for holding a fluid, such as a shaving gel or lotion, and a discharge opening 11 in or near the shaving head 3. The reservoir 10 communicates with the discharge opening 11. A fluid drive structure for driving the fluid from the reservoir 10 to and out of the discharge opening 11 during a dispensing operation is also part of the dispensing structure 30. When empty, the reservoir 10 can be replaced.

Figure 2:
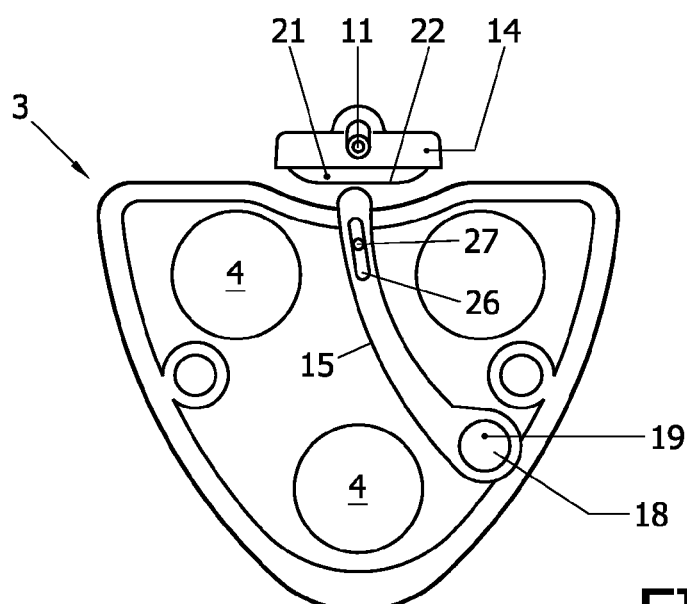
FIG. 2 is a cross-sectional view of a shaving head of the appliance shown in FIG. 1.

According to the present example illustrated in FIGS. 1 and 2, the fluid drive structure includes a diaphragm pump 14, an actuator 15 for activating the pump 14, a secondary motor 16 and transmission members 15, 17, 19, 27. The diaphragm pump 14 is shown in more detail in FIGS. 2 and 4. In the pump 14, a pump chamber 21 is located, which has a flexible wall portion 22, a one-way inlet (not shown) connecting to the reservoir 10 and a one-way outlet (not shown) connecting to the discharge opening 11. The actuator 15 is formed by a push rod of which one end is coupled to an excenter 18 on a drive shaft 19 coupled to the secondary motor 16 and the other end is provided with a slotted guide hole 26 in which a fixed guide pin 27 engages. In operation, this configuration transforms rotary motion of the drive shaft 19 into a reciprocating movement of the push member 15, causing the flexible wall portion 22 of the pump chamber 21 to be alternatingly compressed and allowed to flex back. This generates a repetitive cycle of overpressure during which the chamber 21 is emptied and sub-pressure during which the chamber 21 is filled with fresh fluid from the reservoir 10.

In the illustrated embodiment, the actuator 15 is driven by a secondary motor 16 and via transmission 17, which are both separate from the main motor 6 and the transmission driving the cutters of the shaver. In an alternative embodiment, the actuator and cutters are coupled so as to be driven by a single motor. Such a single motor is preferably combined with two sets of transmission means, with independently adjustable transmission ratios, so that the rotation speed of the cutters 4 and the frequency of the actuator 15 may be independently varied with respect to each other.

Figure 5:
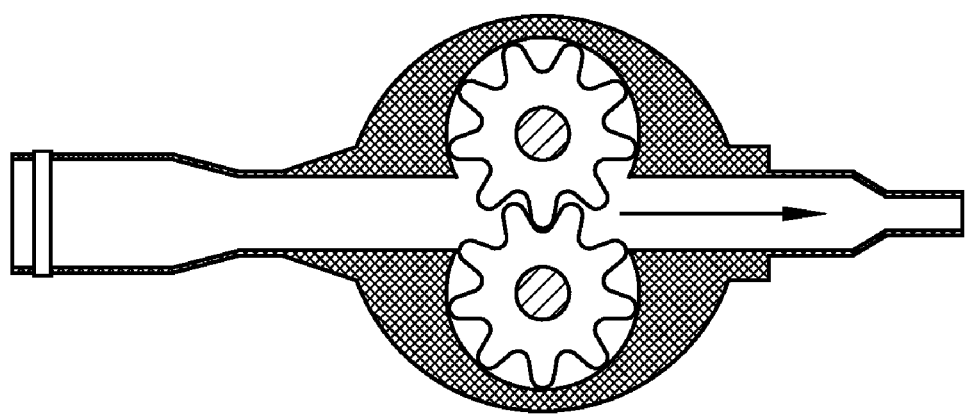
FIG. 5 shows an alternative embodiment of a pump.

Instead of via the actuator 15, power can alternatively be transmitted to the pump by means of, for example, a piezoelectric element 25 placed against the flexible wall portion 22 of the pump chamber 21 (FIGS. 4A and 4B). This element 25 is designed in such a way that, in the powered condition, it bends towards the pump chamber 22, as illustrated in FIG. 4B, thereby depressing the wall portion 22 and causing pumping action. Alternatively, the piezoelectric element 25 may be arranged to act on a flexible part of the reservoir 10 or a cartridge disposed therein (not shown). Piezoelectric means 25 have good dynamic characteristics (short response time), can be accurately controlled by a suitable electric control signal and require little space, and may therefore be advantageously applied in relatively small appliances, such as a shaver. Instead of the diaphragm pump 14, other types of pumps can be employed, such as a gear pump as shown in FIG. 5 or a piston pump.

Also, instead of a pump, drive means may be employed, such as pressurizing means for maintaining a pressure in the fluid reservoir that drives fluid to the discharge opening, in combination with a valve restricting the flow of fluid to the discharge opening. A combination of, for instance, a pump and a valve is also possible, so that the dosage of fluid may be controlled by adjusting the pump frequency, the stroke and/or the valve opening or the return flow via a return conduit.

The drive structure further includes a control unit 20 for controlling the rate at which fluid is dispensed in accordance with a predetermined dispensing rate/time profile $S_x$. The control unit 20 is preferably formed by an electronic circuitry. The circuitry may be suitable to adjust the rate/time $S_x$ and/or may include a memory for storing one or more dispensing rate/time profiles $S_x$. The electronic circuitry may form a microcontroller for also controlling other functions of the appliance. It is equally possible to provide the circuitry as an application specific integral circuit (ASIC).

Figure 3:
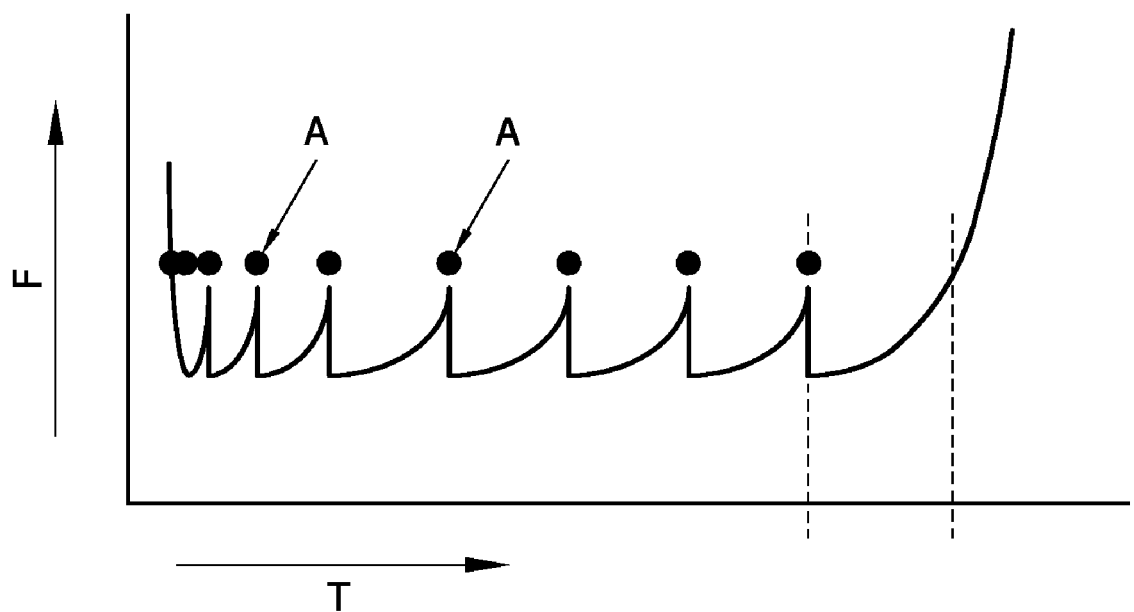
FIG. 3 is a graph illustrating the influence of the application of a shaving gel on the friction between the shaving head and the skin of a user.

The dispensing rate/time profiles $S_x$ may be established on the basis of theoretical knowledge or empirical data regarding the influence of the dispensing rate on the treatment carried out with the personal care appliance. An example of such knowledge is for instance reflected in FIG. 3, showing how the friction F between a shaving head 3 and the skin of a consumer changes over time T in response to application of shaving gel during a shaving session. As can be seen in FIG. 3, at the start of the shaving session the friction is relatively high. After application of a first dose of shaving gel (indicated by a black dot A) the friction drops quite considerably and then gradually increases back to its initial value. Upon reaching this initial value, a new dose of shaving gel is applied, causing the friction level to drop and rise again. As this pattern is repeated, it appears that the time interval before returning to the original high friction level increases during the shaving session to a more or less constant value. From this information a dispensing rate/time profile can be derived that will keep the friction at a satisfactorily low level during the shaving session. This dispensing rate/time profile $S_x$ may have an initially high fluid dispensing rate $\Phi$ that gradually decreases towards a constant lower value, as illustrated by profile $S_1$ in FIG. 6.

Figure 6:
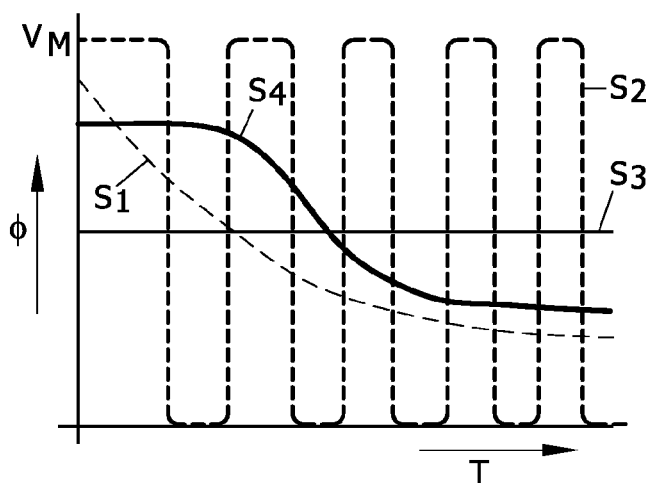
FIG. 6 is a graph in which four alternative examples of dispensing rate/time profiles are shown.

A dispensing rate/time profile $S_1$ can be pre-programmed in the appliance 1 by the manufacturer. However, the required dispensing rate/time profile $S_x$ may differ per situation, for instance depending on the shaving conditions (e.g. the rotation speed of the cutters, the number of cutters, the climate and the type of fluid used) or the user (e.g. the condition of the body part, the treatment habits of the user, such as the frequency of using the appliance, the applied (shaving) force, etc.). To cater to such different situations and/or users, a number of dispensing rate/time profiles may be stored in the control unit 20. The most appropriate dispensing rate/time profile $S_x$ may for instance be selected by means of a humanly operable interface, such as a touch screen, a switch or a speech recognition unit. Several examples of conceivable dispensing rate/time profiles $S_{1-4}$ are depicted in FIG. 6.

Figure 7:
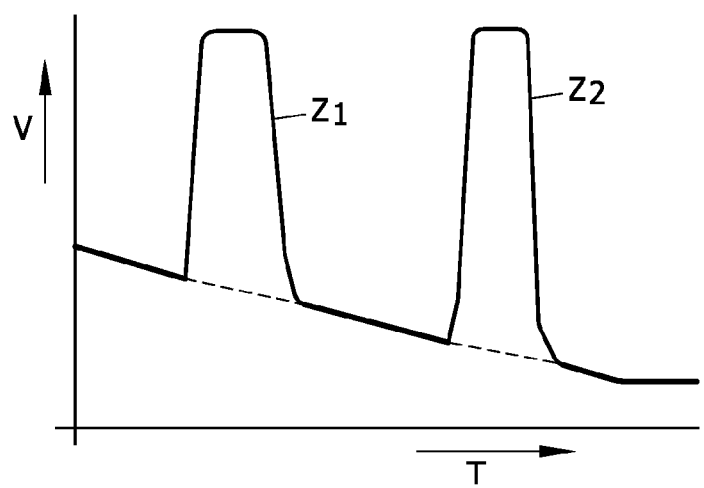
FIG. 7 is a graph depicting a voltage V applied to the secondary motor as a function of time.

FIG. 7 depicts an example in which two squirts $Z_1$ and $Z_2$ are dispensed in addition to the dispensing according to a gradually decreasing dispensing rate/time profile.

The squirts may be of a predetermined duration, triggered when the dispensing structure is operated for producing a squirt of the fluid. It is also possible that the duration of the spurting is dependent on the duration the operating interface is operated, for instance by keeping a push button depressed.

Hence, the fluid drive structure drives the fluid to be dispensed from the reservoir to and out of the discharge opening 11 in accordance with a dispensing rate/time profile $S_x$ and can spurt during said dispensing operation by squirting the fluid to and out of the discharge opening 11 at a squirting rate higher than the rate at which the fluid is dispensed in accordance with the dispensing rate/time profile $S_x$.

When dispensing rate/time profiles $S_x$ are applied for which it holds that the dispensing rate $\phi$ does not exceed 2 ml/minute, which is a practical value for current glide agents for shaving, it has been found that the dispensing rate (p during spurting is preferably between 0.5-100.0 ml/minute. Furthermore, it has been found that the average dispensing rate during spurting is preferably at least five times, and more preferably at least ten times higher than the average dispensing rate during the non-spurting dispensing operation.

It is possible to arrange the fluid drive structure for effectuating the spurting in reaction to a user command. This can for example be realized with a user switch that is connected to the control means 20. The user is then able to decide when a squirt of the fluid is desired.

It is also possible to arrange the fluid drive structure for automatically starting the spurting at one or more predetermined moments during a dispensing period. An advantage is that a squirting of fluid is automatically caused at a pre-known, suitable moment. Such a moment may for example be substantially at the beginning of a dispensing operation period, since then the skin usually is still completely fluid free.

It is furthermore possible to arrange the fluid drive structure for automatically starting one or more spurtings in reaction to the detection of a condition of the treatment and/or of the body part. To this end, a sensor 31 (see FIG. 1) may be provided for detecting such a condition. If the appliance is a shaver, such a condition may be that the friction between the body part and treatment parts 4 of the appliance 1 exceeds a predetermined level. The squirting of the fluid is then automatically initiated at a suitable moment, which depends on the condition of the treatment and/or of the body part. For example, it is to be expected that during shaving under a shower a dry-skin situation will be detected less often than during shaving at a washbasin.

In particular in embodiments in which pressure in the fluid reservoir drives the fluid or in which the dispensing is controlled using a return flow channel instead of a pump, a valve may be arranged for allowing the increased spurting dispensing rate for squirting the fluid to the treatment area.

The dispensing of the fluid according to a predetermined dispensing rate/time profile $S_x$ may also be achieved by supplying voltage pulses to the secondary motor 16. This is shown in FIG. 6 (profile $S_2$) and in FIG. 8, which depicts the voltage V applied to the secondary motor 16 as a function of time T. By changing the duration of the time intervals between the different pulses at maximum voltage $V_M$ and/or the duration of the pulses, different profiles $S_x$ may be obtained.

Figure 8:
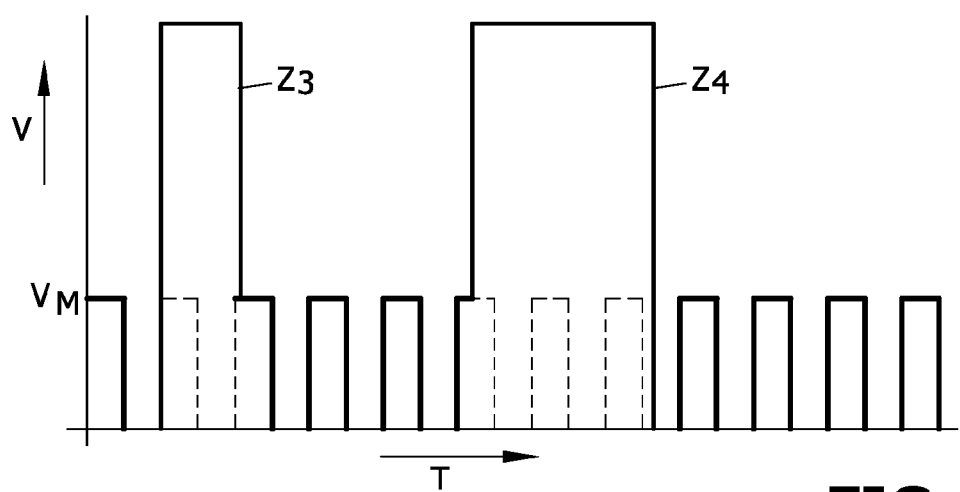
FIG. 8 is another graph depicting a voltage V applied to the secondary motor as a function of time.

When the dispensing structure is operated for producing a squirt of the fluid, instead of applying voltage pulses, an increased voltage is supplied to the secondary motor 16 continuously, but for a limited period of time. This period of time is substantially longer than the duration of an individual pulse. However, compared with the duration of a total dispensing operation, this time period is only small. In this way the fluid drive structure 30 temporarily spurts during a dispensing operation. This spurting results in the fluid being squirted out of the reservoir 10 at a temporarily increased dispensing rate. This squirting of additional fluid will terminate after the spurting has ended. Then, the dispensing of fluid according to the still active dispensing rate/time profile $S_x$ is resumed. FIG. 8 shows the occurrence of two squirts $Z_3$ and $Z_4$ temporarily overriding a dispensing rate/time profile. In the present example, the voltage during spurting is higher than the maximum voltage during normal dispensing. However, the voltage during spurting may also be the same as, or even lower than, during normal dispensing, in which case the increased dispensing rate during squirting is achieved only by the continuous application of that voltage.

Within the framework of the present invention, various modifications other than those described above are possible. For instance, the data processor may be adapted for determining the dispensing rate/time profile in accordance with squirt commands inputted during at least one previous treatment. If a large number of squirt commands is inputted, the dispensing rate/time profile to be applicable during a next treatment may for instance be increased and it may also be taken into account whether the squirt commands have predominantly been inputted during an early stage or during a late stage of the treatment. If no or very few squirt commands have been inputted, the dispensing rate/time profile to be applicable during a next treatment may for instance be lowered.

These and comparable variations are understood to fall within the scope of the invention as outlined in the following claims.

The invention claimed is:

1. An appliance for personal care, comprising:
   a structure for performing a treatment;
   a dispensing structure for automatically dispensing a fluid, wherein the dispensing structure comprises,
      a fluid reservoir,
      a discharge opening, and
      a fluid drive structure for driving the fluid to be dispensed from the reservoir to and out of said discharge opening in accordance with a dispensing rate/time profile ($S_x$), the fluid drive structure being arranged for spurting, at a predetermined time during a dispensing operation an amount of the fluid to and out of the discharge opening at a squirting rate higher than the dispensing rate at which the fluid is dispensed in accordance with said dispensing rate/time profile ($S_x$); and
   a data processor for determining the dispensing rate/time profile ($S_x$) in accordance with signals received from a sensor, the signals representing operating conditions picked up by the sensor.

2. An appliance according to claim 1, wherein the fluid drive structure is arranged in such a way that, during spurting, the fluid is dispensed at a rate at least five times higher than an average dispensing rate during non-spurting dispensing operation.

3. An appliance according to claim 1, wherein the fluid drive structure is arranged for automatically spurting in response to being activated.

4. An appliance, comprising:
   a structure for performing a treatment;
   a dispensing structure for automatically dispensing a fluid, wherein the dispensing structure comprises,
      a fluid reservoir,
      a discharge opening, and
      a fluid drive structure for driving the fluid to be dispensed from the reservoir to and out of said discharge opening in accordance with a dispensing rate/time profile ($S_x$), the fluid drive structure being arranged for spurting, at a predetermined time during a dispensing operation an amount of the fluid to and out of the discharge opening at a squirting rate higher than the dispensing rate at which the fluid is dispensed in accordance with said dispensing rate/time profile ($S_x$);
   a sensor for sensing a condition of the treatment or of a body part to be treated, wherein the fluid drive structure communicates with said sensor and is arranged for automatically spurting in response to a condition meeting a predetermined requirement, signalled by said sensor; and
   a data processor for determining the dispensing rate/time profile ($S_x$) in accordance with signals received from the sensor, the signals representing operating conditions picked up by the sensor.

5. An appliance according to claim 4, wherein the appliance is a shaver and wherein said sensor is adapted for sensing friction between a skin to be treated and the shaver.

6. An appliance according to claim 1, wherein the fluid drive structure comprises a pump communicating with the reservoir and with the discharge opening for driving the fluid from the reservoir to the discharge opening.

7. An appliance according to claim 1, further comprising a control valve downstream of the reservoir, for controlling fluid flow from the reservoir to the discharge opening, said control valve being arranged for selectively allowing said spurting.

8. An appliance according to claim 1, wherein the personal care appliance is a hair removing apparatus, wherein the fluid to be dispensed is one of a shaving lotion or gel.

9. An appliance according to claim 1, wherein the personal care appliance is a brush, wherein the fluid to be dispensed is one of a toothpaste or polishing agent.

10. An appliance according to claim 1, wherein the personal care appliance is a hairstyler, wherein the fluid to be dispensed is one of steam, a fixing agent, wax or a dye.

\* \* \* \* \*